United States Patent
Edelson et al.

(10) Patent No.: US 7,727,523 B2
(45) Date of Patent: Jun. 1, 2010

(54) METHOD FOR SUPPRESSING IMMUNE SYSTEM RESPONSE TO TRANSPLANTED TISSUE OR CELLS

(75) Inventors: Richard Leslie Edelson, Westport, CT (US); Carole Berger, Bronx, NY (US); Michael Girardi, Madison, CT (US)

(73) Assignee: Yale University, New Haven, CT (US)

( * ) Notice: Subject to any disclaimer, the term of this patent is extended or adjusted under 35 U.S.C. 154(b) by 765 days.

(21) Appl. No.: 10/290,802

(22) Filed: Nov. 8, 2002

(65) Prior Publication Data

US 2003/0133914 A1    Jul. 17, 2003

Related U.S. Application Data

(63) Continuation-in-part of application No. 10/217,856, filed on Aug. 13, 2002, now Pat. No. 7,625,557.

(60) Provisional application No. 60/312,004, filed on Aug. 13, 2001.

(51) Int. Cl.
*A01N 1/02* (2006.01)
*A61M 37/00* (2006.01)
*C12N 5/08* (2006.01)

(52) U.S. Cl. .................... 424/93.71; 424/93.7; 435/2; 435/372; 604/4.01; 604/6.03; 604/6.08

(58) Field of Classification Search .............. 435/2, 435/372; 424/93.7, 93.71; 604/4.01, 6.03, 604/6.08
See application file for complete search history.

(56) References Cited

U.S. PATENT DOCUMENTS

| 4,321,918 | A | 3/1982 | Clark |
| 4,838,852 | A | 6/1989 | Edelson et al. |
| 6,524,855 | B2 | 2/2003 | Edelson et al. |
| 6,596,275 | B1 | 7/2003 | Bartholeyns et al. |
| 6,602,709 | B1 | 8/2003 | Albert et al. |
| 6,800,300 | B1 | 10/2004 | Miller et al. |
| 2002/0051771 | A1 | 4/2002 | Bolton et al. |
| 2002/0114793 | A1 | 8/2002 | Edelson et al. |
| 2003/0133914 | A1* | 7/2003 | Edelson et al. ............ 424/93.7 |
| 2005/0084966 | A1* | 4/2005 | Edelson et al. ............ 435/372 |

FOREIGN PATENT DOCUMENTS

| WO | WO 97/34472 | 9/1997 |
| WO | WO 00/62818 | 10/2000 |

OTHER PUBLICATIONS

Greinix, et al. Successful Use of Extracorporeal Photochemotherapy in the Treatment of Severe Acute and Chronic Graft-Versus-Host Disease, Blood, vol. 92, No. 9, 1998, pp. 3098-3104.
Greinix, et al. Extracorporeal Photochemotherapy in the Treatment of Severe Steroid-Refractory Acute Graft-Versus-Host Disease: A Pilot Study, Blood, vol. 96, No. 7,, 2000, pp. 2426-2431.
Barr, et al. Photopheresis for the Prevention of Rejection in Cardiac Transplantation, The New England Journal of Medicine, 1998, pp. 1744-1751.
Yamane, et al. Suppression of Anti-Skin-Allograft Response by Photodamaged Effector Cells—The Modulating Effects of Prednisolone and Cyclophosphamide, Transplantation, 1992, pp. 119-124.
Perez, Induction of a Cell-Transferable Suppression of Alloreactivity by Photodamaged Lymphocytes, Transplantation, 1992, pp. 896-903.
Perez, DNA Associated with the Cell Membrane is Involved in the Inhibition of the Skin Rejection Response in the Inhibition of the Skin Rejection Response Induced by Infusions of Photodamaged Alloreactive Cells that Mediate Rejection of Skin Allograft, Photochemistry and Photobiology, vol. 55, No. 6, 1992, pp. 839-849.
Cohen, et al. $CD4^+CD25^+$ Immunoregulatory T Cells: New Therapeutics for Graft-Versus-Host Disease, The Rockefellar University Press, vol. 196, No. 3, Aug. 5, 2002, pp. 401-406.

(Continued)

*Primary Examiner*—David A. Saunders
(74) *Attorney, Agent, or Firm*—McCarter & English, LLP

(57) ABSTRACT

Methods are provided for suppressing the immune system response in recipients of transplanted organs, tissues or cells. An extracorporeal quantity of blood from the intended transplant recipient is treated to induce monocytes contained in the blood to differentiate and form dendritic cells. The maturation of the dendritic cells is truncated at a stage where the dendritic cells can inactivate T cell clones which would otherwise generate an undesired immune system response. The immature dendritic cells can be directly administered to the transplant recipient, or the dendritic cells can be co-incubated with the bone marrow or stem cell preparation, prior to transplantation, in order to suppress or eliminate anti-recipient donor T cells contaminating the bone marrow or stem cell preparation. The methods can be used to suppress graft versus host disease in recipients of transplanted bone marrow or stem cells, or to suppress rejection of transplanted organs or tissue.

11 Claims, No Drawings

OTHER PUBLICATIONS

Chambers, The expanding world of co-stimulation: the two-signal model revised, Trends in Immunology, vol. 22, No. 4, Apr. 2001, pp. 217-223.
Hoffmann, et al. Donor-type CD4+CD25+ Regulatory T Cells Suppress Lethal Acute Graft-Versus-Host Disease after Allogeneic Bone Marrow Transplantation, The Rockefeller University Press, vol. 196, No. 3, Aug. 5, 2002, pp. 389-399.
Rossi, M. et al., Plasmacytoid Dendritic Cells: Do They Have a Role in Immune Responses After Hematopoietic Cell Transplantation? Human Immunology Dec. 2002, vol. 63, No. 12, pp. 1194-1200.
Heshmati, F. Mechanisms of Action of Extracorporeal Photochemotherapy Transfusion and Apheresis Science Aug. 2003, vol. 29, No. 1, pp. 61-70, Abstract.
Ying G et al: "Tricyclic antidepressants prevent the differentiation of monocytes into macrophage-like cells in vitro." *Cel Biol Toxicol.* 2002; 18(6):425-37.
Beaudoin L et al: "NKT cells inhibit the onset of diabetes by impairing the development of pathogenic T cells specific for pancreatic beta cells." *Immunity.* Dec. 2002;17(6):725-36.
Kitazawa T et al: "Studies on delayed systemic effects of ultraviolet B radiation on the induction of contact hypersensitivity, 3. Dendritic cells from secondary lymphoid organs are deficient in interleukin-12 production and capacity to promote activation and differentiation of T helper type 1 cells." *Immunology.* Feb. 2000;99(2):296-304.
Tang A et al: "Inhibition of epidermal Langerhans cell function by low dose ultraviolet B radiation. Ultraviolet B radiation selectively modulates ICAM-1 (CD54) expression by murine Langerhans cells." *J Immunol.* May 15, 1991;;146(10):3347-55.
Shen W et al: "Ganglioside GD1a impedes lipopolysaccharide-induced maturation of human dendritic cells." *Cell Immunol.* Dec. 2002;220(2):125-33.
Lateef Z et al: "Orf virus-encoded interleukin-10 inhibits maturation, antigen presentation and migration of murine dendritic cells." *J Gen Virol.* May 2003;84(Pt 5):1101-9.
Shurin MR et al: "Inhibition of CD40 expression and CD-40-mediated dentritic cell function by tumor-derived IL10." *Int J Cancer.* Sep. 1, 2002;101(1):61-8.
Semnani RT et al: "Filarial antigens impair the function of human dendritic cells during differentiation." *Infect Immun.* Sep. 2001;69(9):5813-22.
Chung F: "Anti-inflammatory cytokines in asthma and allergy: interleukin-10, interleukin-12, interferon-gamma." *Mediators Inflamm.* Apr. 2001;10(2):51-9. Links .
Hackstein H et al: "Aspirin inhibits in vitro maturation and in vivo immunostimulatory function of murine myeloid dendritic cells." *J Immunol.* Jun. 15, 2001;166(12):7053-62.
Komi J et al: "Non-steroidal anti-oestrogens inhibit the differentiation of synovial macrophages into dendritic cells." *Rheumatology (Oxford)* Feb. 2001;40(2):185-91.
Moore KW et al: "Interleukin-10 and the interleukin-10 receptor." *Annu Rev Immunol.* 2001;19:683-765.
Bernstein SH et al: "A randomized phase II study of BB-10010: a variant of human macrophage inflammatory protein-1 alpha for patients receiving high-dose etoposide and cyclophosphamide for malignant lymphoma and breast cancer." *BR J Haematol.* Dec. 1997;99(4):888-95.
Askenase PW et al: "Gamma delta T cells in normal spleen assist immunized alpha beta T cells in the adoptive cell transfer of contact sensitivity. Effect of Bordetella pertussis, cyclophosphamide, and antibodies to determinants on suppressor cells." *J Immunol.* Apr. 15, 1995;154(8):3644-53.
De Smedt T et al: "Effect of interleukin-10 on dendritic cell maturation and function." *Eur J Immunol.* May 1997;27(5):1229-35.
Hirohata S: "Suppression of human B cell responsiveness by CD4+ T cells does not involve CD95-CD95 ligand interactions." *Cell Immunol.* Nov. 1, 1997;181(2):182-91.
Estry DW et al: "A comparison of the fibrinogen receptor distribution on adherent platelets using both soluble fibrinogen and fibrinogen immobilized on gold beads." *Eur J Cell Biol.* Apr. 1991;54(2):196-210.
Blank K et al: "Self-immobilizing recombinant antibody fragments for immunoaffinity chromatography: generic, parallel, and scalable protein purification." *Protein Expr Purif.* Mar. 2002;24(2):313-22.
Garlie NK et al: "T cells activated in vitro as immunotherapy for renal cell carcinoma: characterization of 2 effector T-cell populations." *J Urol.* Jul. 2001;166(1):299-303.
Foger N. et al: "CD44 supports T cell proliferation and apoptosis by apposition of protein kinases." *Eur J Immunol.* Oct. 2000;30(10):2888-99.
Hanau D et al: "A method for the rapid isolation of human epidermal Langerhans cells using immunomagnetic microspheres." *J Invest Dermatol.* Sep. 1988;91(3):274-9.
Thomas R et al: "Human peripheral blood dendritic cell subsets. Isolation and characterization of precursor and mature antigen-presenting cells." *J. Immunol.* Nov. 1, 1994;153(9):4016-28.
Yanagihara S et al: "EBI1/CCR7 Is a New Member of Dendritic Cell Chemokine Receptor That is Up-Regulated Upon Maturation." *The Journal of Immunology* 1998, 161: 3096-3102.
Li B et al: "Pretreatment of recipients with mitomycin-C-treated dendritic cells induces significant prolongation of cardiac allograft survival in mice." *Transplantation Proceedings* vol. 34, Issue 8, Dec 2002, pp. 3426-3428.
Jiga L et al: "Generation of tolerogenic dendritic cells by treatment with mitomycin c: inhibition of allogeneic T-cell response is mediated by downregulation of ICAM-1, CD80, and CD86." *Transplantation.* vol. 77(11), Jun. 15, 2004, pp. 1761-1764.
Tanigawa T et al: "Injection of mitomycin-C-treated spleen cells induces donor-specific unresponsiveness to cardiac allografts in rats [experimental transplantation]." *Transplantation.* vol. 67(5), Mar. 15, 1999, pp. 653-658.
Albert M et al: "Immature Dendritic Cells Phagocytose Apoptotic Cells via $\alpha_v\beta_5$ and CD36, and Cross-present Antigens to Cytotoxic T Lymphocytes" *J. Exp. Med.* vol. 188, Nov. 7, Oct. 5, 1998 1359-1368.
Morel A et al: "Regulation of major histocompatability complex case II synthesis by interleukin-10." *Immunology* 2002 106 229-236.
Kakumu S et al: "Decreased function of peripheral blood dendritic cells in patients with hepatocellular carcinoma with hepatitis B and C virus infection." *Journal of Gastroenterology and Hepatology*, 2000 15, 431-436.
Coates P et al: "Human myeloid dendritic cells transduced with an adenoviral interleukin-10 gene construct inhibit human skin graft rejection in humanized NOD-scid chimeric mice." *Gene Therapy.* 2001 8, 1224-1233.
Corinti S et al: "Regulatory Activity of Autocrine IL-10 on Dendritic Cell Functions." *J Immunol.* 2001, 166:4312-4318.
Griffin M et al: "Dendritic cell modulation by $1\alpha,25$ dihydroxyvitamin $D_3$ and its analogs: A vitamin D receptor-dependent pathway that promotes a persistent state of immaturity in vitro and in vivo." *PNAS* Jun. 5, 2001 vol. 98, No. 12, 6800-6805.
Canning M et al: "$1\alpha,25$-Dydroxyvitamin $D_3$ ($1,25(OH)_2 D_3$) hampers the maturation of fully active immature dendritic cells from monocytes." *European Journal of Endocrinology* 2001 145 351-357.
Shurin MR et al: "Inhibition of CD40 expression and CD-40 mediated dentritic cell function by tumor-derived IL-10." *Int J Cancer.* Sep. 1, 2002;101(1):61-68.
Simon JC et al: "UVB-Irradiated Dendritic Cells Induce Nonproliferating, Regulatory Type T Cells." *Skin Pharmacol Appl Skin Physiol* 2002:15:330-334.
International Search Report.
Supplementary Partial European Search Report.
Berger et al. Induction of human tumor-loaded dendritic cells, Int. J. Cancer, 2001, vol. 91, pp. 438-447.
Brooks, CG., "The effects of cell density, incubation temperature, syngeneic serum and syngeneic red blood cells on mouse lymphocyte responses in vitro", J. Immunol Methods, Dec 9, 1975 (2) 171-84.
Supplemental European Communication dated Dec. 22, 2006 for Application No. 02 750 483.6 - 1222.
Fay et al. Dendritic Cell Immunotherapy of Metastic Malanoma Using CD34+ Hemotopietic Progenitor-Derived Dendritic Cells (CD34-DC) Induced Immune Responses to Melanoma Antigen and Resulted in Clinical Regression of Metastatic Disease. Blood, Nov. 16, 2000.

Greinix et al. Extracorporeal Photochemotherapy in the Treatment of Severe Steroid-Refractory Acute Graft-Versus-Host Disease: A Pilot Study, Blood, vol. 96, No. 7, 2000, pp. 2426-2431.

International Preliminary Examination Report in International Application No. PCT/US02/25703 mailed May 10, 2005.

Kanada, D., et al., "Photopheresis Monocytes Produce Cytokines that Induce Monocyte-to-Dendritic Cell Maturation During Overnight Incubation", Journal of Investigative Dermatology, vol. 117, No. 2, May 12, 2001 (2001-05) p. 535, Abstract 873.

Oliven, A., et al., "Extracorporeal Photopheresis: A review", Blood Reviews, vol. 15, Jun. 2001 (2001-06), pp. 103-108.

Purrott, R.J. et al. Cellular and Molecular Life Sciences, vol. 37, No. 4, Apr. 1982, pp. 407-408; abstract.

* cited by examiner

METHOD FOR SUPPRESSING IMMUNE SYSTEM RESPONSE TO TRANSPLANTED TISSUE OR CELLS

PRIOR APPLICATIONS

This application is a continuation-in-part of U.S. patent application Ser. No. 10/217,856, filed on Aug. 13, 2002 now U.S. Pat. No. 7,625,557, which claims the benefit of U.S. Provisional Application No. 60/312,004, filed on Aug. 13, 2001.

FIELD OF THE INVENTION

The present invention is directed to methods of suppressing the immune system response in recipients of transplanted organs, tissue or cells. In one embodiment, methods are provided for reducing the effects of graft versus host disease (GVHD) in individuals receiving stem cell or bone marrow transplants. In another embodiment, methods are provided for suppressing the immune response in individuals receiving transplanted organs or tissue to reduce the likelihood of rejection of the transplanted organs or tissue by the transplant recipient.

BACKGROUND OF THE INVENTION

Transplantation of organs, tissue or cells from one genetically distinct person (donor) to another (recipient) is hindered by the recipient's immunologic rejection of the donated organs or cells. This rejection phenomenon is understood to involve both cellular and humoral mechanisms, mediated respectively by T cells and antibodies. The recipient's immune system targets distinguishing histocompatibility antigens on the transplanted cells. Except in rare cases, the donor's histocompatibility antigens will not match exactly the recipient's histocompatibility antigens, and the recipient's immune system attacks the incompatible donor organs or cells.

With respect to immunologically mediated rejection, the most potent of the histocompatibility antigens are the major histocompatibility complexes (MHC) known as the human leukocyte antigens, HLA-A, HLA-B and HLA-C. Although originally defined by their presence on the cell membranes of human leukocytes, they have long been recognized to be present on virtually all of the nucleated cells of the human body. Since each person receives genes encoding one set of these antigens from each parent, human cells typically express six major HLA antigens. In addition to the major histocompatibility antigens, there are several minor histocompatibility antigens.

When tissue or cells are transplanted, it is desirable to match, to the maximum extent possible, the histocompatibility antigens of the donor and the recipient. The best immunologic match between donor and recipient is between identical twins, since they share the same six major HLA antigens. In addition, identical twins also share the same minor histocompatibility antigens, and therefore organs or cells transplanted from one identical twin to the other are immunologically tolerated. In the far more common situation in which the donor and recipient are not genetically identical, some level of immunologic rejection of transplanted tissue regularly occurs. To minimize this rejection and permit survival of the engrafted tissue, efforts are routinely made to find the best match between donor and recipient. If an identical twin is not available, the next best choice is typically a non-identical sibling of the recipient sharing the same six major HLA antigens, a situation which occurs on the average in one out of four siblings. Such a six out of six HLA match between siblings is preferable to a six out of six match between unrelated individuals, because the matched siblings will also more likely share at least some minor histocompatibility antigens inherited from their common parents. Yet, because they are not identical siblings, there is a high probability of some difference in the minor histocompatibility antigens, and the donor and recipient will almost certainly be sufficiently distinct in terms of cellular antigens that some level of rejection will occur following transplantation of tissue from one sibling to another.

The adverse reactions following transplantation of an organ or tissue from one genetically distinct individual to another can be profoundly dangerous. The primary adverse reaction is immunologic rejection of the transplanted organ or tissue. If the organ is life-sustaining, such as a heart, liver or lung, the destruction of that organ may lead directly to the death of the patient. In other circumstances, such as rejection of insulin producing pancreatic islet cells or kidneys, the quality of life of the recipient may be devastated by the tissue rejection. In order to prevent or limit the rejection, patients typically receive a combination of immunosuppressive drugs, which introduce their own major side effects. These drugs are usually globally immunosuppressive, thereby greatly increasing the susceptibility of the recipient to serious infections, often by organisms against which an uncompromised immune system would readily defend. The individual immunosuppressive drugs each have their own set of other adverse effects, especially when used in the dosages necessary to inhibit rejection of transplanted organs. For example, high doses of prednisone precipitate diabetes mellitus and hypertension, while simultaneously causing demineralization of supporting bones. Another commonly used immunosuppressive drug, cyclosporine A, has major toxic effects on the kidney. Globally immunosuppressive treatments also increase the susceptibility of transplant recipients to opportunistic infections, against which normal individuals have strong defenses.

These adverse effects have stimulated searches for therapies that can more selectively suppress the rejection of transplanted tissue, while leaving the remainder of the immune system intact and not injuring other important organs. An especially promising approach has been the use of a conventional Photopheresis device to deliver the immunotherapy generally referred to herein as "Transimmunization" to prevent or reverse rejection of transplanted organs. Depending on the circumstances, the therapeutic impact of the Transimmunization can be enhanced by following the conventional Photopheresis step with an overnight incubation phase, prior to returning the treated cells to the patient. Transimmunization may be accomplished using a Photopheresis apparatus, although Transimmunization may also be accomplished without the use of a Photopheresis apparatus, using other methodology.

A controlled trial comparing conventional Photopheresis plus conventional immunosuppression with conventional immunosuppression alone in the prevention of rejection of transplanted hearts was reported by Barr et al., Photopheresis for the prevention of rejection in cardiac transplantation, *New England Journal of Medicine*, Vol. 339, No. 4, 1744-51, Dec. 10, 1998. That study revealed that the addition of Photopheresis to the conventional immunosuppressive regimen quite significantly and safely reduced the number of rejection episodes, thereby markedly diminishing the need for dangerous boosting of the levels of toxic conventional immunosuppressive drugs. Similarly, in Greinix et al., Successful use of extracorporeal photochemotherapy in the treatment of severe acute and chronic graft-versus-host disease, *Blood*, Vol. 92, No. 9, 3098-3104, 1998, and in Greinix et al., Extracorporeal photochemotherapy in the treatment of severe steroid-refractory acute graft-versus-host disease: a pilot study, *Blood*, Vol. 96, No. 7, 2426-31, 2000, the authors describe testing which revealed that Photopheresis was particularly effective in reversing the adverse effects (known as graft-versus-host-disease or GVHD) following transplantation of bone marrow or stem cells.

One mechanism that is involved in the efficacy of Photopheresis has been recently deciphered. The flat plastic ultraviolet exposure system, a component of the Photopheresis apparatus, can cause the transformation of blood monocytes to dendritic antigen presenting cells (dendritic cells) as a result of the forces imposed on the monocytes as they flow past the plastic surface in a conventional Photopheresis apparatus. Since the therapeutic benefits resulting from the use of these dendritic cells are caused by the transfer of tissue antigens to dendritic cells capable of immunization of the patient against these antigens, the immunotherapy is referred to as "Transimmunization." Therefore, Transimmunization is a treatment that can, in one embodiment, be accomplished with a Photopheresis apparatus. Alternatively, the Transimmunization treatment may be performed using any other appropriate device having plastic channels which can induce differentiation of monocytes into dendritic cells. One important difference between the Transimmunization process described herein and conventional Photopheresis is the recognition that the necessary tissue antigens can best be delivered to the new dendritic cells by overnight ex vivo incubation, prior to return to the patient of the antigen loaded dendritic cells.

In Photopheresis, a photoactivatable agent, such as 8-methoxypsoralen (8-MOP), is activated by exposure to ultraviolet A (UVA) in extracorporeally circulated blood, causing the 8-MOP to form photo adducts with pyrimidine bases of DNA and tyrosine containing cytoplasmic proteins. The positive clinical sequelae caused by Photopheresis result from the patient's immunologic response to the reinfused treated blood. The resulting immune response can, in the best responders, lead to the selective suppression or even elimination of the pathogenic clone(s).

As stated above, it has more recently been discovered that the passage of the blood through the plastic ultraviolet exposure chamber of the Photopheresis device can stimulate the conversion of blood monocytes to dendritic antigen presenting cells (DC), the most potent initiators of cellular immune reactions. Two phenomena contribute to the clinical success of Transimmunization. In certain situations, it is desirable to produce a positive immunologic reaction or immunization against disease causing cells which are distinguished from their normal counterparts by their surface display of distinctive molecular targets which can be targeted immunologically. One such situation is cancer, in which the malignant cells display distinctive tumor antigens. In other situations, it is desirable to suppress an immunologic reaction which actually causes the disease. Those situations include immunologic rejection of a transplanted organ or graft-versus-lost disease (GVHD), in which stem cell preparations transplanted from a donor to a recipient include donor T cells which then recognize the recipient's tissues as "foreign", proliferate to form many copies of themselves in the recipient and dangerously attack the normal cells of the recipient.

In the cancer situation, the malignant cells may be damaged so that they will be ingested by the newly formed DC, which are then permitted to develop into mature DC which subsequently present the distinctive antigens of the pathogenic cells to a responding immune system, thereby generating a "positive" immunologic reaction capable of inhibiting or destroying a cancer. The CD8 (and probably also CD4) T cell responses caused or enhanced by this treatment can often be sustained for long periods of time. As described in U.S. patent application Ser. No. 09/928,855, now U.S. Pat. No. 6,607,722, the process can be refined to maximize ingestion of apoptotic pathogenic T cells by newly formed DC and thereby maximize the strength of the anti-cancer immunologic reactions generated.

However, a variation of the same procedure can also be used to selectively suppress undesirable immunologic reactions, such as organ transplant rejection or GVHD, through the suppressive actions of DC that have remained immature. Unlike mature DC, immature DC transmit specific suppressive signals to T cells, because the immature DC have not yet developed the arsenal of membrane molecules capable of stimulating strong positive immunologic responses. For example, immature DC are deficient in costimulatory molecules, such as B7.1 and B7.2, which can contribute to the delivery of positive signals to responsive T cells. Instead of causing positive, or immunizing responses, these immature DC can selectively suppress reactions against precisely those antigens which they have ingested, processed and presented on their surface. Studies in an experimental model of conventional Photopheresis revealed the capacity of that treatment to selectively suppress rejection of transplanted tissue. Specifically, when skin was transplanted from a donor black mouse to a genetically completely distinct white mouse, the transplanted skin was completely rejected within 14 days. This was anticipated, since the donor and recipient mice differed in terms of histocompatibility antigens to a level equivalent to a six out six mismatch in humans and since skin is the most immunogenic solid organ. Following the rejection of the transplanted skin, the recipient mouse was sacrificed and its spleen, containing markedly expanded clones of those T cells causing the rejection, as well as tissue monocytes, were brought into single cell suspension. Then, in a system devised to mimic conventional photopheresis, the suspended T cells were exposed in a petri dish to UVA activated 8-MOP and then returned intravenously to a mouse genetically identical to the original recipient, thereby immunizing this new mouse against the clones of T cells involved in the rejection of the transplanted skin.

This new mouse then received new skin transplants: one from the same original donor strain and another from a third mouse strain completely unrelated to either of the other two strains. Instead of being rejected within 14 days as before, the transplanted skin from the original donor strain now survived intact for the full 42 days of the experiment. In contrast, the simultaneously transplanted skin from the third unrelated strain was rejected within the 14 days. The selective suppression of the rejection of the skin graft could be transferred to another set of mice, genetically identical to the original recipient, by transfusion of recipient T cells. These results demonstrated that the experimental model of Photopheresis led to donor specific suppression of the rejection of the transplanted skin and that this suppression was mediated by selectively suppressive T cells induced by the procedure. These tests are reported in more detail in Yamane et al., Suppression of anti-skin-allograft response by photodamaged effector cells—the modulating effects of prednisone and cyclophophamide, *Transplantation*, Vol. 54, 119-124, No. 1, July 1992; Perez et al., Induction of a cell-transferable suppression of alloreactivity by photodamaged lymphocytes, *Transplantation*, Vol. 54, 896-903, No. 5, November 1992; Perez et al., DNA associated with the cell membrane is involved in the inhibition of the skin rejection response induced by infusions of photodamaged alloreactive cells that mediate rejection of skin allograft, *Photochemistry and Photobiology*, Vol. 55, 839-849, No. 6, 1992.

Paradoxically, when the experiment was altered so that the donor strain differed from the recipient strain by only minor histocompatibility antigens, the transplanted skin could be kept intact on the recipient for only 21 days. This was longer than in untreated controls, but only half as long as when skin from the completely unrelated strain was transplanted to prepared recipients. Although puzzling at the time, it appears that the stronger the reaction that is being suppressed, the more effective it is. This is probably due to the preferential sensitivity of high affinity T cells, more readily generated by potent immune reactions, to be suppressed directly by the immature DC produced in the experimental Photopheresis procedure. Importantly, this finding suggests that the Transimmunization process described below may be most effective in preventing rejection of transplanted organs when the donor and recipient are mismatched by one or more HLA antigens. Accordingly, Transimmunization may dramatically augment the donor pool of transplantable tissue. The modification of Transimmunization which is described in this application will further augment the donor pool of transplantable tissue, by enhancing the suppressive effects of Transimmunization.

Methods for suppressing the immune response of individuals to transplanted tissue or cells using the Transimmunization procedure in combination with skin grafts between transplant recipients and donors have been described previously in pending U.S. patent application Ser. No. 10/217,856. The present invention relates to methods of suppressing the immune response of individuals to transplanted tissue or cells using a modified Transimmunization procedure to induce formation of dendritic cells, and truncating the maturation of the dendritic cells at a stage where they will inactivate selected T cells which would otherwise participate in GVHD or in rejection of a transplanted organ or tissue.

Immature dendritic cells may be used to suppress undesired immune system responses in individuals receiving transplanted bone marrow, stem cells, organs or tissues. Immature dendritic cells can preferentially suppress immune responses due to their relative deficiency in costimulatory molecules, such as CD-80 and CD-86 (also known as B7.1 and B7.2 respectively). In order for an antigen presenting dendritic cell to stimulate positive immune responses from antigen-specific T cells, two signals must be transmitted from the antigen presenting dendritic cell to the antigen-specific T cell. A first signal is transmitted from the antigen presented on the surface of the dendritic cell to the T cell via the binding of the antigen with a complementary surface T cell receptor. The second signal is transmitted by costimulatory molecules on the surface of the dendritic cell. If the antigen signal is transmitted in the absence of the costimulatory signal, the antigen-specific T cell is inactivated or eliminated, rather than being stimulated to produce a positive immunologic response to cells displaying the transmitted antigens. It is known that immature dendritic cells are deficient in costimulatory molecules, and therefore transmit negative or suppressive signals to those T cells having receptors for the presented antigens. Accordingly, dendritic cells may be produced having a truncated maturation, and the immature dendritic cells can be used to suppress the response of antigen specific T cells in transplant recipients.

Cancer patients are often prepared for bone marrow/stem cell transplants from genetically distinct individuals by first receiving large doses of chemotherapy to accomplish two goals: diminution of the tumor burden and weakening of the immune system so that the transplanted cells will not be quickly rejected. This level of preparation is itself life threatening, since the cancer patient's own bone marrow is largely destroyed by the preparative chemotherapy. If the transplanted cells do not take and ultimately reconstitute the patient's bone marrow, the patient will succumb to infections, anemia, hemorrhage, etc. When the bone marrow/stem cell transplant does successfully reconstitute the patient's immune system, that immune system is repopulated by the cells of the donor. These donor cells then recognize the recipient's tissue as foreign and attack (reject) the recipient's own organs in a process called graft versus host disease (GVHD). Most prominently attacked in this resulting GVHD are the skin (which can slough), the liver (which can fail) and the intestinal tract (which can cease to function properly and hemorrhage). Life-saving reversal or suppression of GVHD is quite difficult with conventional treatments, which are usually quite toxic.

Remarkably, in recent years, it has become clear that a controllable level of GVHD may be of great benefit to the cancer patient. Since the donor cells react against recipient histocompatibility antigens, and since the residual cancer cells are also recipient cells bearing the patient's histocompatibility antigens, a certain level of "graft-versus-tumor" reaction or GVTR commonly accompanies the undesirable other components of GVHD. Those cancer patients who survive GVHD following bone marrow/stem cell transplants appear to have an improved survival from their cancer, since recurrences are less frequent. Therefore, a fine line exists between the toxic effects of GVHD and the beneficial ones of GVTR. In an ideal situation, a treatment could suppress GVHD while leaving a partial GVTR, directed at those weaker antigens which distinguish the malignant cells from the benign cells of the recipient. The methods of the present invention may be used to inactivate donor T cells which would otherwise attack the recipient's healthy tissues, while leaving intact T cells which attack tumor cells displaying a different set of antigens.

In the organ transplantation situation, the recipient's T cells attack the transplanted organ, as the cells of the transplanted organs display antigens that are not identical to the antigens present in the recipient's cells. It would be desirable to find a treatment that could inactivate the recipient's T cells from attacking cells displaying the donor's antigens, while not effecting the ability of the recipient's T cells from recognizing and attacking infectious microbes or other disease causing agents.

SUMMARY OF THE INVENTION

The present invention provides methods of suppressing the immune system response in recipients of transplanted organs, tissues or cells, thereby enhancing the likelihood that the transplanted tissue or cells will be immunologically tolerated by the recipient. In a first embodiment of the invention, which is particularly useful for bone marrow or stem cell transplants, graft-versus-host disease ("GVHD") is suppressed by treating an extracorporeal quantity of blood from the intended recipient of a stem cell or bone marrow transplant to induce monocytes contained in the extracorporeal quantity of the recipient's blood to differentiate into recipient dendritic cells. Following formation of recipient dendritic cells, the extracorporeal quantity of blood is further treated to truncate the maturation of the recipient dendritic cells. The maturation of the recipient dendritic cells is truncated at a stage where a substantial portion of the recipient dendritic cells will function to deactivate donor T cells from attacking the organs or tissue of the transplant recipient.

In one embodiment of the invention, after maturation of the recipient dendritic cells is truncated, by physical means (such as, for example, γ-irradiation) or by cytostatic chemotherapeutic agents (such as, for example, mitomycin C or cyclophosphamide), the recipient's immature dendritic cells are administered to the recipient prior to bone marrow stem cell transplantation. The recipient dendritic cells are then present in the recipient's system to inactivate those clones of the donor's T cells which would otherwise attack the healthy cells of the transplant recipient. Alternatively, the immature recipient dendritic cells can be frozen and administered to the recipient after bone marrow stem cell transplantation.

In another embodiment of the invention, after maturation of the recipient dendritic cells is truncated, the recipient's immature dendritic cells are combined with bone marrow or stem cell preparations from the intended transplant donor containing passenger or contaminating T cells from the donor. The recipient's immature dendritic cells are co-incubated with the donor's T cell containing bone marrow or stem cells for a sufficient time to allow the recipient immature dendritic cells to inactivate or eliminate those clones of the donor's T cells which would otherwise attack the healthy cells of the transplant recipient. Following co-incubation, the dendritic cell/bone marrow mixture is administered to the intended transplant recipient, to reconstitute the patient's immune system, while minimizing or eliminating the chance for development of GVHD.

In another embodiment, which is particularly useful for organ or tissue transplants, an individual receiving an organ or tissue transplant is treated to suppress the recipient's immune system response to the transplanted organ or tissue. In this embodiment, an extracorporeal quantity of the transplant recipient's blood is treated to induce blood monocyte differentiation into recipient dendritic cells. The maturation of the recipient dendritic cells is truncated by physical means (such as, for example, γ-irradiation) or by cytostatic chemotherapeutic agents (such as, for example, mitomycin C or cyclophosphamide) at an immature stage where the recipient dendritic cells are capable of inactivating or eliminating those recipient T cell clones capable of attacking the transplanted donor tissue. To load the newly formed recipient dendritic cells with antigens from the donor, a quantity of the donor's blood is removed, and the leukocytes contained in the donor's blood are damaged in such a manner that they are induced to undergo apoptosis (programmed cell death) or necrosis (frank cell death). The recipient immature dendritic cells are combined with the donor's damaged leukocytes and incubated for a sufficient period of time to allow the recipient dendritic cells to internalize and process the donor leukocytes and present donor antigens at their surface. The incubated blood cells, including the immature recipient dendritic cells loaded with tissue antigens from the donor, are then administered to the intended transplant recipient. The immature recipient dendritic cells interact with recipient T cells to inactivate or eliminate those recipient T cells capable of attacking cells displaying the donor's distinctive tissue antigens, thereby reducing or eliminating the immune system response of the recipient against the transplanted organ or tissue.

Among the advantages of the methods of the present invention is that the use of globally immunosuppressive drugs in transplant recipients may be reduced or eliminated, thereby reducing or eliminating the adverse health effects associated with immunosuppressive drugs. Another advantage of the methods of the present invention is that the incidence and severity of GVHD in bone marrow/stem cell transplant recipients may be greatly reduced. A further advantage of the methods of the present invention is that the pool of potential transplant donors may be expanded. Other advantages of the methods of the present invention will be readily apparent to those skilled in the art based on the detailed description of preferred embodiments set forth below.

DETAILED DESCRIPTION OF PREFERRED EMBODIMENTS

The present invention relates to methods of suppressing the immune system response in recipients of transplanted organs, tissues or cells. The methods comprise inducing differentiation of monocytes into dendritic cells in an extracorporeal quantity of the blood of the intended transplant recipient. Maturation of the dendritic cells is truncated at a stage where a substantial portion of the dendritic cells are deficient in costimulatory molecules and can inactivate T cells which would otherwise attack the recipient's healthy tissue or the transplanted tissue or cells. In the case of a bone marrow or stem cell transplant, the dendritic cells will signal the donor T cells produced by, or included with, the transplanted bone marrow or stem cells to tolerate the recipient's organs and tissue, thereby reducing or eliminating graft-versus-host disease (GVHD) in the transplant recipient. In the case of an organ transplant, the dendritic cells will diminish or eliminate the likelihood that recipient T cells will reject the transplanted organ.

Methods for Bone Marrow/Stem Cell Transplantation

In a first embodiment of the invention, which may be especially useful in the case of bone marrow or stem cell transplantation, the intended transplant recipient is treated to reduce or eliminate GVHD following the bone marrow or stem cell transplantation. As used herein and in the claims, "transplant preparation" means a sample of bone marrow and/or stem cells from the transplant donor contaminated with donor T cells, some of which are anti-recipient tissue antigen donor T cells.

An extracorporeal quantity of blood is obtained from the intended transplant recipient and the blood is treated to induce differentiation of monocytes contained in the recipient's blood into functional dendritic cells, which are referred to herein as "recipient dendritic cells." Monocyte differentiation is induced by causing the monocytes to flow through a device having narrow plastic channels, such as for example the narrow plastic channels in a conventional Photopheresis apparatus. Methods for inducing differentiation of monocytes into functional dendritic cells, have been described previously in U.S. patent application Ser. Nos. 09/294,494, now abandoned, and 10/066,021, both titled "Methods for Inducing the Differentiation of Monocytes Into Functional Dendritic Cells and Immunotherapeutic Compositions Including Such Dendritic Cells", the entire contents of both of which are expressly incorporated herein by reference. The recipient dendritic cells will naturally display on their surface the tissue type human leukocyte antigens typical of the intended transplant recipient. As described below, this antigen display may be enhanced as a result of the ingestion of apoptotic recipient leukocytes by the recipient dendritic cells.

Maturation of the recipient dendritic cells is truncated, by physical or chemical methods, at a stage where the immature dendritic cells preferentially induce immune suppression. Immature dendritic cells induce suppression of the immune system response because of their relative deficiency in costimulatory molecules, such as CD-80 and CD86. It is known that, in order to stimulate positive immune responses from antigen-specific T cells, two signals must be transmitted from the antigen-presenting dendritic cell to the specific T cell. The first signal is transmitted to the T cell by its binding (via its surface T cell receptor) of the presented antigen on the surface of the dendritic cell. The second signal is transmitted by costimulatory molecules also on the surface of the dendritic cell. If only the antigen signal is transmitted, in the absence of the costimulatory signal, the antigen-specific T cell is inactivated or eliminated, rather than stimulated to produce a positive immunologic response. It is known that immature dendritic cells are deficient in costimulatory molecules and therefore transmit negative or suppressive signals to the T cells, which have T cell receptors specific for the presented antigens. Accordingly, as discussed below, by truncating the maturation of the recipient dendritic cells at an appropriate stage, the recipient dendritic cells can be used to inactivate or eliminate those anti-donor antigen-specific T cells contained in, or produced by, the donor bone marrow, thereby preventing T cell attack of the organs or tissue of the bone marrow transplant recipient, as occurs in GVHD.

Techniques for truncating the maturation of dendritic cells are well known to those skilled in the art. For example, exposure of the immature dendritic cells to appropriate doses of γ-irradiation will truncate the maturation of the dendritic cells, while leaving the dendritic cells functional. Alternatively, dendritic cell maturation can be truncated by exposing the dendritic cells to cytostatic drugs (such as, for example, mitomycin C or cylcophosphamide) or certain cytokines (such as, for example, IL-10). The invention is not limited in this regard, and any means known to those skilled in the art may be used to truncate the maturation of the dendritic cells while leaving the dendritic cells functional.

Dendritic cell maturation is preferably truncated at a stage in which the dendritic cells are deficient in co-stimulatory molecules CD-80 and CD-86. These marker molecules increase in concentration at the dendritic cell surface with increasing maturity of the dendritic cells. The dendritic cell maturation stage can be determined using any appropriate method known to those skilled in the art. For example, fluorescein-tagged monoclonal antibodies that bind selectively to CD-80 and CD-86 may be added to the treated blood, and the bound fluorescein-tagged monoclonal antibodies can be measured using a cytofluorograph. It should be recognized that it will not be necessary to measure the maturation of the dendritic cells by this method in every case. Rather, an appropriate incubation time period for dendritic cell formation and maturation can be initially determined for a particular device or type of device used to induce monocyte differentiation, and the determined incubation time can be used as the standard time for performing the method described herein using the device. It should be understood that, if desired, the dendritic cells may be frozen after they have been treated to truncate maturation and stored for later use.

In one embodiment of the invention, after maturation of the recipient dendritic cells is truncated, the immature dendritic cells are returned to the recipient prior to administration of the transplant preparation. The relatively large population of recipient immature dendritic cells present in the recipient can interact in vivo to inactivate the clones of donor T cells in the transplant preparation which would otherwise attack the recipient's healthy tissue cells. Alternatively, the recipient immature dendritic cells can be frozen and administered to the recipient together with or after administration of the transplant preparation to suppress GVHD. If desired, an aliquot of the recipient immature dendritic cells can be administered to the recipient prior to administration of the transplant preparation, and one or more aliquots of recipient immature dendritic cells can be administered after administration of the transplant preparation.

In another embodiment of the method of the invention, after the recipient dendritic cells have been treated to truncate maturation, the immature recipient dendritic cells are combined with a transplant preparation comprising a sample of bone marrow and/or stem cells from the intended transplant donor containing a subpopulation of anti-recipient tissue antigen donor T cells. The anti-recipient donor T cells are a relatively small population of the cells in the transplant preparation because, prior to introduction to the transplant recipient, the donor T cells have not been stimulated by the recognition of recipient antigens to proliferate and form expanded clones whose T cell members are primed to attack the recipient's cells. It should be understood that, if desired, the dendritic cells may be frozen after they have been treated to truncate maturation and stored for later use.

The immature dendritic cells and the transplant preparation containing donor T cells are co-incubated for a sufficient period of time to permit the immature recipient dendritic cells to selectively inactivate or eliminate the donor T cells which would otherwise attack the recipient's cells after transplantation. The immature recipient dendritic cells inactivate or eliminate the donor T cell capacity to attack the recipient's cells which exhibit the same recipient antigens displayed by the recipient dendritic cells. Preferably, incubation will take place for a period of from 12 to 24 hours. However, longer or shorter incubation times may be used, provided the incubation time is sufficient to allow an adequate number of dendritic cells to contact and suppress or eliminate the donor anti-recipient T cells.

Co-incubation of the recipient dendritic cells and the transplant preparation containing donor T cells is performed using techniques known to those skilled in the art. In a preferred embodiment, incubation is performed at approximately 37 degrees Centigrade in a standard incubator containing a gaseous environment having approximately 5% carbon dioxide and approximately 95% oxygen, with only trace amounts of other gases.

Following coincubation of the immature recipient dendritic cells with the donor T cell containing transplant preparation, the mixture of recipient dendritic cells and donor T cell containing transplant preparation is administered to the transplant recipient. Preferably, the transplant recipient will have received preparative chemotherapy before the mixture is administered to preclude the rejection of the transplanted donor bone marrow. The transplanted donor bone marrow and/or stem cells reconstitutes the recipient's reconstitutes the immune system. Because the anti-recipient type donor T cells contained in the transplant preparation have been deactivated, GVHD in the recipient is reduced or eliminated.

In the optimal situation, the immature recipient dendritic cells will inactivate or eliminate only those donor T cells which attack cells displaying the antigens of the recipient's tissue, while not affecting the ability of anti-tumor donor T cells to attack tumor cells which display a different set of tumor antigens or to reconstitute the immune system's capacity to defend against the broad spectrum of other antigens, such as those typical of infective microbes. The invention is not limited in this regard, however, and the method may be used to suppress GVHD without providing any benefit in treating tumor cells.

While the invention is not limited to any particular mechanism by which the dendritic cells act to induce immunologic tolerance to transplanted bone marrow or stem cells, it is believed that the immature dendritic cells transmit inhibitory signals to antigen-specific T cells because the immature dendritic cells are relatively deficient in costimulatory molecules. The transplant recipient receives immature dendritic cells which are formed from the recipient's blood and which display the recipient's antigens. The maturation of the dendritic cells has been truncated at a stage where the immature dendritic cells are deficient in a co-stimulatory molecules CD-80 and CD-86 (also known as B7.1 and B7.2 respectively). The antigen-loaded, immature dendritic cells transmit suppressive or tolerogenic signals to the donor T cells in the transplant preparation that have the antigen-specific T cell receptors (TCR) that will recognize and bind to the relevant antigens.

Because the immature dendritic cells are relatively deficient (as compared to mature dendritic cells) in co-stimulatory molecules CD-80 and CD-86, the responding donor T cell is stimulated to express on its surface CTLA-4, which avidly binds to the minimally present CD-80 and CD-86 on the surface of the immature dendritic cells. The binding of specific T cells to the antigen presented by the dendritic cell in the presence of minimal expression co-stimulatory molecules cause the antigen-specific donor T cell to become a selectively inhibitory T cells that expresses CTLA-4. These selectively inhibitory T cells also express CD4 and CD25. The selectively inhibitory donor T cell inhibits other donor T cells form attacking the recipient's cells, thereby inhibiting GVHD in the bone marrow transplant recipient.

Co-incubation of the immature recipient dendritic cells with the donor T cell containing transplant preparation stimulates formation of selectively inhibitory CD4(+) CD25(+) CTLA-4(+) donor T cells, thereby reducing or eliminating GVHD. CD4 is a marker of helper/inducer T cells, and CD25 is the receptor for a T cell growth factor known as Interleukin-2. The subset of T cells identified by the simultaneous presence of surface CD4 and CD25 can act to suppress the activity of those T cells which cause GVHD, transplanted organ rejection and autoimmune diseases (such as lupus or rheumatoid arthritis). The suppressive effect of the CD4(+) CD25(+) T cells may be enhanced by the presence of Interleukin-10 (IL-10). Accordingly, IL-10 may be added to the immature recipient dendritic cells either before, during or after co-incubation with the donor T cell containing bone marrow.

It should be recognized that it is not a requirement or limitation of the method of the present invention that the immature dendritic cells react with the donor T cells precisely as described herein, and that there may be other aspects of the interaction between the immature dendritic cells and the donor T cells which are involved, in whole or in part, in the suppression of GVHD. For example, in certain circumstances the immature dendritic cells may directly inhibit or even delete auto-reactive T cells, rather than operating through intermediary suppressive T cells.

In another embodiment of the present invention, after maturation of the dendritic cells is truncated, the dendritic cells are further treated to remove any dendritic cells in the treated blood which may have matured beyond the desired stage for use in GVHD suppression. After the blood has been treated to induce monocyte differentiation, incubated, and treated to truncate dendritic cell maturation, the dendritic cells are passed through a media to remove mature dendritic cells. The media displays one or more antibodies that will selectively bind to molecules displayed by dendritic cells which have matured beyond the desired stage for use in the GVHD treatment.

Preferably, the dendritic cells are passed through a packed column. The column may be packed with materials, such as resin beads, which have at their surface one or more antibodies that selectively bind to mature dendritic cells. The mature dendritic cells selectively bind to the antibodies, while the immature dendritic cells pass through the column, resulting in a composition having a high percentage of immature dendritic cells which can be used in the methods of the present invention.

Production of Dendritic Cells

As noted above, the Transimmunization process for inducing monocyte differentiation into dendritic cells has been generally described previously. As modified for use in the method of the present invention, the modified Transimmunization process results in the production of recipient dendritic cells which can be further treated and used to suppress GVHD or rejection of transplanted organs or tissue. In the methods described herein, the modified Transimmunization process is performed by obtaining an extracorporeal quantity of the transplant recipient's blood and treating the blood to induce differentiation of monocytes into immature recipient dendritic cells. The recipient dendritic cells are subsequently further treated to truncate their maturation in a state in which they preferentially induce immune suppression, rather than the positive immune responses which can be produced by mature dendritic cells. As discussed above, it is known to those skilled in the art that exposure of the immature dendritic cells to appropriate doses of γ-irradiation will truncate the maturation of the dendritic cells, while still leaving them functional. Other approaches to keeping the recipient dendritic cells immature, such as exposure to cytostatic drugs (such as, for example, mitomycin C or cyclophosphamide) or to certain cytokines (e.g., IL-10), are also known and could be substituted when appropriate for γ-irradiation. The invention is not limited in this regard, and any appropriate method for truncating the maturation of dendritic cells without destroying the functionality of the cells may be used.

Monocyte differentiation may be induced by exposing monocytes contained in an extracorporeal quantity of the transplant recipient's blood to physical perturbation, in particular to the forces exerted on the monocytes by their sequential adhesion to and release from plastic surfaces as they flow through a narrow plastic channel, such as the narrow plastic channel in a conventional Photopheresis device. In a preferred embodiment, a white blood cell concentrate is prepared from an extracorporeal quantity of the transplant recipient's blood in accordance with standard leukapheresis practice using a leukapheresis/Photopheresis apparatus of the type known to those skilled in the art. The white blood cell concentrate includes monocytes, lymphocytes and some red blood cells and platelets. Two billion white blood cells can typically be collected during leukapheresis. Assuming that monocytes comprise from about 2% to about 50% of the total white blood cell population collected, approximately 40 million to 1 billion monocytes are present in the white blood cell concentrate. The median monocyte percentage is approximately 20%, so commonly about 400 million monocytes will be in the white blood concentrate collected via leukapheresis.

Following separation by leukapheresis, monocyte differentiation is induced by pumping the blood cell concentrate through a device having a plurality of plastic channels. Preferably, the plastic channels have a diameter of between about 0.5 mm and 5.0 mm. Most preferably, a conventional Photopheresis apparatus having a channel diameter of 1 mm or less is used. The narrow channel configuration of the Photopheresis apparatus maximizes the surface area of plastic to which the blood cell concentrate is exposed as it flows through the Photopheresis apparatus. The invention is not limited in this regard, however, and any appropriate device having plastic channels may be used to induce monocyte differentiation. For example, the extracorporeal quantity of blood may be passed through a column containing plastic beads or some other device or means to channel flow through the column. Also, the extracorporeal quantity of blood may be caused to flow through the plastic channels by gravity, by pressure or by any other technique which will cause the blood to flow through the plastic channels.

While the invention is not limited to any particular mechanism of monocyte differentiation, it is believed that monocytes in the blood cell concentrate are attracted to the plastic channel walls of the Photopheresis apparatus, and the monocytes adhere to the channel walls. The fluid flow through the channel imposes shearing forces on the adhered monocytes that cause the transiently and incompletely adherent monocytes to be released from the plastic channel walls. Accordingly, as the monocytes pass through the Photopheresis apparatus, they may undergo numerous episodes of transient adherence to and release from the plastic channel walls. These physical forces send activation signals though the monocyte cell membrane, which results in induction of differentiation of monocytes into functional dendritic cells. Preliminary evidence suggests that interaction of monocyte β-glycoprotein with the plastic surface may contribute to the monocyte entry into the dendritic cell maturational pathway. Therefore, it may be possible to induce monocyte-to-dendritic cell maturation by direct interaction with monocyte P-glycoprotein, without use of a plastic flow system.

After monocyte differentiation to dendritic cells has been induced, the treated blood is incubated for a sufficient period of time to allow the dendritic cells to develop to the desired stage of maturity prior to truncation of maturation. Incubation of the recipient dendritic cells is performed using techniques known to those skilled in the art. In a preferred embodiment, incubation is performed at approximately 37 degrees Centigrade in a standard incubator containing a gaseous environment having approximately 5% carbon dioxide and approximately 95% oxygen, with only trace amounts of other gases.

Inducing monocytes to form dendritic cells by the plastic transient adherence flow method offers several advantages for treatment related to organ or tissue transplants. Because all of the recipient dendritic cells are formed from the monocytes contained in the transplant recipient's blood within a very short period of time, the recipient dendritic cells are all of approximately the same age. By creating dendritic cells with a relatively narrow age profile, the modified Transimmunization process provides an enhanced number of immature recipient dendritic cells which can be used to suppress selected immune system responses. Because the immature recipient dendritic cells are deficient in certain co-stimulatory surface molecules, such as those of the B7 family, they send suppressive signals to antigen-responsive T cells with which they develop cell-to-cell contact. Because the immature recipient dendritic cells produced during the modified Transimmunization procedure are all the same age, this approach can provide an abundance of immature recipient dendritic cells capable of producing dominant suppression of the otherwise potent immune reactions which can cause rejection of transplanted organs.

If desired, the presentation of recipient antigens on the surface of the recipient dendritic cells may be enhanced by loading the recipient dendritic cells with apoptotic or necrotic T cells contained in the recipient's blood. Apoptosis or necrosis is induced in T cells contained in the recipient's blood, the recipient dendritic cells and apoptotic or necrotic T cells are co-incubated for a sufficient period of time to allow the dendritic cells to phagocytize the apoptotic T-cells, and the immature, antigen-loaded recipient dendritic cells can be used to selectively suppress GVHD or organ transplant rejection. Apoptosis, i.e. programmed cell death, leads to display on the surface of the dying cell of membrane molecules for which immature dendritic cells have receptors, thereby facilitating the ingestion of the dying cells (or their fragments) and the processing of their antigens by dendritic cells. Recently, it has become generally recognized that antigens of cells that die by routine necrosis (as well as their fragments) can also be internalized and processed by dendritic cells. Accordingly, it should be understood that the methods described herein can be performed using cells that have been rendered either apoptotic or necrotic.

T cells contained in the extracorporeal quantity of the recipient's blood may be rendered apoptotic or necrotic by any method known to those skilled in the art. For example, apoptosis may be induced by exposing the T cells to ultraviolet energy, x-ray irradiation or γ-irradiation. Also, heat shock, cold shock, hydrostatic pressure or hypotonic solutions can lethally damage T cells or other cells in ways, such as cellular necrosis, that lead to their uptake and processing by dendritic cells, in analogous fashion that can also trigger the same immune phenomena. If desired, combinations of these methods may be used to render T cells apoptotic or necrotic.

In a particularly preferred embodiment, T cells in the extracorporeal quantity of the recipient's blood are rendered apoptotic in the Photopheresis apparatus as the monocytes are induced to form recipient dendritic cells by the physical forces they experience as they flow through the narrow plastic channels in the Photopheresis apparatus. A photoactivatable agent capable of inducing apoptosis in the T cells is added to the blood cell concentrate prior to passage through the Photopheresis apparatus, and the blood cell concentrate is irradiated as it passes through the Photopheresis apparatus to render the T cells apoptotic. By rendering the T cells apoptotic in the Photopheresis apparatus, these cells are immediately available to be phagocytized as the monocytes are differentiating to form dendritic cells. This method of treating the blood to simultaneously induce monocyte differentiation and apoptosis of T cells contained in the blood has been described in detail in U.S. patent application Ser. No. 10/217,856, the contents of which are incorporated herein in their entirety.

Method for Organ Transplantation

In another embodiment of the invention, a method is provided to suppress the immune response of an individual receiving a transplantation of an organ or tissue from a different person. An extracorporeal quantity of blood from the intended transplant recipient is treated using the modified Transimmunization process described above to induce differentiation of blood monocytes into recipient dendritic cells.

An extracorporeal quantity of blood leukocytes is obtained from the intended transplant donor. The donor leukocytes can be obtained by performing standard leukapheresis on an extracorporeal quantity of blood obtained from the transplant donor. The donor leukocytes are injured in such a manner that they become apoptotic (undergo programmed cell death) or become necrotic. The donor leukocytes may be injured using any technique known to those skilled in the art, such as for example by irradiating the donor leukocytes with γ-radiation, or exposing the donor leukocytes to ultraviolet-activated psoralen or visible light-activated porphyrins, followed by exposure to light, such as in a photopheresis device as described above. Alternatively, the donor leukocytes can be damaged by cytostatic drugs, such as mitomycin C or cyclophosphamide or by physical forces, such as hydrostatic pressure.

The immature recipient dendritic cells and the inactivated donor leukocytes are combined and co-incubated for a sufficient period of time to permit the recipient dendritic cells to process the inactivated donor leukocytes and present antigens from the donor T cells at the surface of the recipient dendritic cells. Preferably, the recipient dendritic cells and apoptotic donor leukocytes are coincubated for a period of 12 to 24 hours. Longer or shorter incubation times may be used, provided that the incubation time is sufficient to permit a substantial quantity of the recipient dendritic cells to process apoptotic donor leukocytes. The recipient dendritic cells and the apoptotic donor leukocytes are co-incubated using standard cell incubation equipment and conditions. Preferably, incubation is performed at approximately 37 degrees Centigrade, in an incubator containing approximately 5% carbon dioxide and approximately 95% oxygen.

Following this co-incubation period, which has enabled the loading of the immature newly formed dendritic cells with donor tissue antigens, the maturation of the recipient dendritic cells is truncated at an immature stage. These immature dendritic cells, which are bearing on their surface antigens derived from the donor leukocytes and which are typical of the donor tissue type, will (because of their deficiency in costimulatory molecules) function to inactivate or eliminate those recipient anti-donor T cells capable of attacking the transplanted donor organ. The maturation of the dendritic cells is truncated using techniques known to those skilled in the art, such as those techniques described above.

The donor antigen-loaded immature recipient dendritic cells are then administered to the intended transplant recipient. The recipient dendritic cells will interact with the recipient's T cells that would otherwise be programmed to attack the transplanted organ or tissue. Because the recipient dendritic cells are presenting antigens characteristic of the donor, the recipient dendritic cells will inactivate or eliminate the recipient's anti-donor T cells, which will therefore not proliferate and will not attack the transplanted organ or tissue displaying the donor antigens. This will reduce or eliminate the attack of the recipient's immune system against the transplanted organ or tissue, thereby reducing or eliminating the need for immunosuppressive drugs.

As will be recognized by those of ordinary skill in the art based on the teachings herein, numerous changes and modifications may be made to the above-described invention without departing from its scope as defined in the appended claims. Accordingly, this detailed description of preferred embodiments is to be taken in an illustrative, as opposed to a limiting sense.

We claim:

1. A method for preparing dendritic cells for use in suppressing graft versus host disease in an individual receiving a transplant preparation derived from an intended transplant donor, comprising the steps of:
   (a) treating an extracorporeal quantity of blood from an intended transplant recipient by causing the blood to flow through an apparatus having plastic channels to induce monocytes contained in the blood to differentiate into dendritic cells;
   (b) treating the dendritic cells to truncate the maturation of the dendritic cells at a stage where the dendritic cells are deficient in costimulatory molecules that interact with T cells such that the dendritic cells can induce suppression of an immune system response by treating the dendritic cells using a treatment selected from the group consisting of irradiation with gamma radiation, exposing the dendritic cells to mitomycin C, exposing the dendritic cells to cyclophosphamide, and exposing the dendritic cells to IL-10;
   (c) combining the dendritic cells from the intended transplant recipient with a transplant preparation derived from the intended transplant donor; and
   (d) co-incubating the dendritic cells from the intended transplant recipient with the transplant preparation from the intended transplant donor.

2. The method of claim 1, wherein the step of treating an extracorporeal quantity of blood from the intended transplant recipient comprises causing the blood to flow through an apparatus having plastic channels with a diameter of between about 0.5 mm and about 5.0 mm.

3. The method of claim 1, wherein the step of treating an extracorporeal quantity of blood from the intended transplant recipient comprises causing the blood to flow through an apparatus having plastic channels with a diameter of less than about 1.0 mm.

4. The method of claim 1, wherein the step of treating an extracorporeal quantity of blood from the intended transplant recipient is performed in a Photopheresis apparatus.

5. The method of claim 1, wherein the dendritic cells and the transplant preparation are co-incubated for a period of between about 12 hours and about 24 hours.

6. The method of claim 5, wherein the dendritic cells and the transplant preparation are co-incubated at a temperature of approximately 37 degrees Centigrade in a gaseous atmosphere comprising approximately 5% carbon dioxide and approximately 95% oxygen.

7. The method of claim 1, further comprising the step of treating the dendritic cells after maturation has been truncated to remove dendritic cells which display antigens characteristic of mature dendritic cells.

8. The method of claim 7, wherein the dendritic cells are treated after maturation has been truncated by causing the dendritic cells to flow through a media that displays one or more antibodies that will selectively bind to molecules displayed by mature dendritic cells.

9. The method of claim 8, wherein the media comprises a packed column having resin beads coated with monoclonal antibodies that selectively bind to antigens displayed by mature dendritic cells.

10. The method of claim 1, wherein the dendritic cell maturation is truncated at a stage where the dendritic cells are deficient in costimulatory molecules CD-80 and CD-86.

11. The method of claim 10, wherein the dendritic cell maturation is truncated by exposing the dendritic cells to one of mitomycin C or IL-10.

* * * * *